United States Patent
Hidari et al.

(10) Patent No.: US 11,382,735 B2
(45) Date of Patent: Jul. 12, 2022

(54) STENT GRAFT AND STENT GRAFT INDWELLING DEVICE

(71) Applicant: SB-KAWASUMI LABORATORIES, INC., Kanagawa (JP)

(72) Inventors: Kentaro Hidari, Oita (JP); Toshiyasu Yuba, Tokyo (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 0 days.

(21) Appl. No.: 16/764,408

(22) PCT Filed: Nov. 22, 2018

(86) PCT No.: PCT/JP2018/043123
§ 371 (c)(1),
(2) Date: May 15, 2020

(87) PCT Pub. No.: WO2019/103084
PCT Pub. Date: May 31, 2019

(65) Prior Publication Data
US 2020/0352698 A1  Nov. 12, 2020

(30) Foreign Application Priority Data
Nov. 27, 2017 (JP) .............................. JP2017-227227

(51) Int. Cl.
A61F 2/02 (2006.01)
A61F 2/07 (2013.01)
A61F 2/954 (2013.01)

(52) U.S. Cl.
CPC ................ *A61F 2/07* (2013.01); *A61F 2/954* (2013.01)

(58) Field of Classification Search
CPC .. A61F 2/07; A61F 2/954; A61F 2/958; A61F 2/962; A61F 2/96611;
(Continued)

(56) References Cited

U.S. PATENT DOCUMENTS

2004/0230287 A1* 11/2004 Hartley .................... A61F 2/07
                                                        623/1.12
2005/0131518 A1*  6/2005 Hartley .................. A61F 2/856
                                                        623/1.13
(Continued)

FOREIGN PATENT DOCUMENTS

JP    2007-508067    4/2007
JP    2014-533559    12/2014
(Continued)

OTHER PUBLICATIONS

International Search Report dated Jan. 8, 2019 From the International Searching Authority Re. Application No. PCT/JP2018/043123 and Its Translation of Search Report Into English. (5 Pages).
(Continued)

*Primary Examiner* — Erich G Herbermann

(57) ABSTRACT

The present invention eliminates the need for highly accurate alignment with a branched tubular tissue when implanting a stent graft. A stent graft 30 comprises: a framework section 31; and a tubular graft section 40. A side surface opening 42 that passes through to the lumen of the graft section is provided in one section of a tube wall 41 of the graft section. In the framework section, among the six frame bodies, the frame bodies 34, 35 that are provided facing the side surface opening section have a first frame body structure section Q that is present in the tube wall along the entire circumference, and a second frame body structure section P that is present in the tube wall in a partial region 41A, which excludes the side surface opening section in the circumferential direction of the tube wall.

17 Claims, 9 Drawing Sheets

(58) Field of Classification Search
CPC .............. A61F 2/9662; A61F 2002/072; A61F 2002/075; A61F 2002/077; A61F 2002/9623; A61F 2/9661; A61F 2/02; A61F 2/04; A61F 2/06; A61F 2/064; A61F 2002/061; A61F 2002/065; A61F 2002/067; A61F 2002/068
See application file for complete search history.

(56) References Cited

U.S. PATENT DOCUMENTS

| | | |
|---|---|---|
| 2011/0270378 A1 | 11/2011 | Bruszewski et al. |
| 2011/0319983 A1 | 12/2011 | Zhu et al. |
| 2012/0109279 A1 | 5/2012 | Mayberry et al. |
| 2012/0197383 A1* | 8/2012 | Ivancev .................... A61F 2/07 623/1.13 |
| 2013/0184806 A1 | 7/2013 | Arbefeuille et al. |
| 2014/0114391 A1 | 4/2014 | Tabor |
| 2016/0310216 A1 | 10/2016 | Van Bibber et al. |

FOREIGN PATENT DOCUMENTS

| | | |
|---|---|---|
| JP | 5789867 | 8/2015 |
| WO | WO 2019/103084 | 5/2019 |

OTHER PUBLICATIONS

Supplementary European Search Report and the European Search Opinion dated Jul. 12, 2021 From the European Patent Office Re. Application No. 18880275.5. (9 Pages).

* cited by examiner

STENT GRAFT AND STENT GRAFT INDWELLING DEVICE

TECHNICAL FIELD

The present invention relates to a stent graft and a stent graft indwelling device.

BACKGROUND ART

Conventionally, a branch vessel-compatible stent graft is known as a stent graft used for the treatment of aortic aneurysms and aortic dissections that occur in the aorta (for example, see Patent Document 1). The conventional stent graft described in Patent Document 1 has a framework section referred to as a so-called stent, and a graft section which is fixed to the framework section. The tube wall of the graft section is provided with a side surface opening which is communicated with the lumen of the graft section. In the conventional stent graft, a branch vessel stent graft is connected to the branch section in a state where the conventional stent graft has been placed in the main blood vessel, and the blood flow between the main vessel and the branch vessel is maintained by arranging the branch vessel stent graft inside the branch vessel.

PRIOR ART DOCUMENT

Patent Document

Patent Document 1: Japanese Patent Publication No. 5,789,867

SUMMARY OF THE INVENTION

Problems to be Solved by the Invention

However, when a stent graft is actually implanted, there is a need to implant the stent graft with a high positional accuracy so that the positional deviation between the blood vessel opening of the branch vessel and the side surface opening of the stent graft is minimized. However, because the position of the blood vessel opening of a branch vessel varies from patient to patient, when the blood vessel opening of the branch vessel and the side surface opening of the stent graft are to be precisely aligned, there is a problem that the influence of the technique and experience of the practitioner may become large.

Such a need may also arise with respect to stent grafts intended to be implanted in tubular tissue other than a blood vessel (for example, the digestive tract or the bile duct).

An object of the present invention is to provide a stent graft and a stent graft indwelling device that eliminate the need for highly accurate alignment with a branched tubular tissue when implanting a stent graft.

Means for Solving the Problem

A stent graft of the present invention includes a framework section having a plurality of frame bodies and a tubular graft section that is fixed to the framework section, in which a side surface opening that passes through to a lumen of the graft section is provided in one section of a tube wall of the graft section, the plurality of frame bodies are arranged along a tube axis of the graft section, and the frame body among the plurality of frame bodies that is arranged correspondingly to the side surface opening includes a first frame body structure section that is present in the tube wall along an entire circumference of the tube wall, and a second frame body structure section that is adjacent to the first frame body structure section and is present in the tube wall in a partial region, which excludes the side surface opening in a circumferential direction of thereof.

Furthermore, a stent graft indwelling device of the present invention includes a stent graft of the present invention, in which the stent graft is configured to be capable of expanding in a radial direction.

Effect of the Invention

According to the present invention, as a result of providing the second frame body structure section that is present in the tube wall in a partial region that excludes the side surface opening in the circumferential direction of the tube wall, for example, the tolerance can be increased with respect to positional displacement between the side surface opening of the stent graft, which is implanted at a branch position between a main vessel and a branch vessel, and the opening of the branch vessel, and therefore, the adjustment of the orientation and position of the side surface opening can be simplified.

Furthermore, as a result of providing the first frame body structure section that is adjacent to the second frame body structure section, the strength of the graft section can be further increased, and displacements in the side surface opening caused by blood flow can be suppressed.

Therefore, the need for highly accurate alignment with a branched tubular tissue is eliminated when implanting the stent graft.

DESCRIPTION OF THE EMBODIMENT

Hereinafter, an embodiment of a stent graft indwelling device 1 and a stent graft 30 of the present invention will be described in detail with reference to the drawings.

Figure 1A:
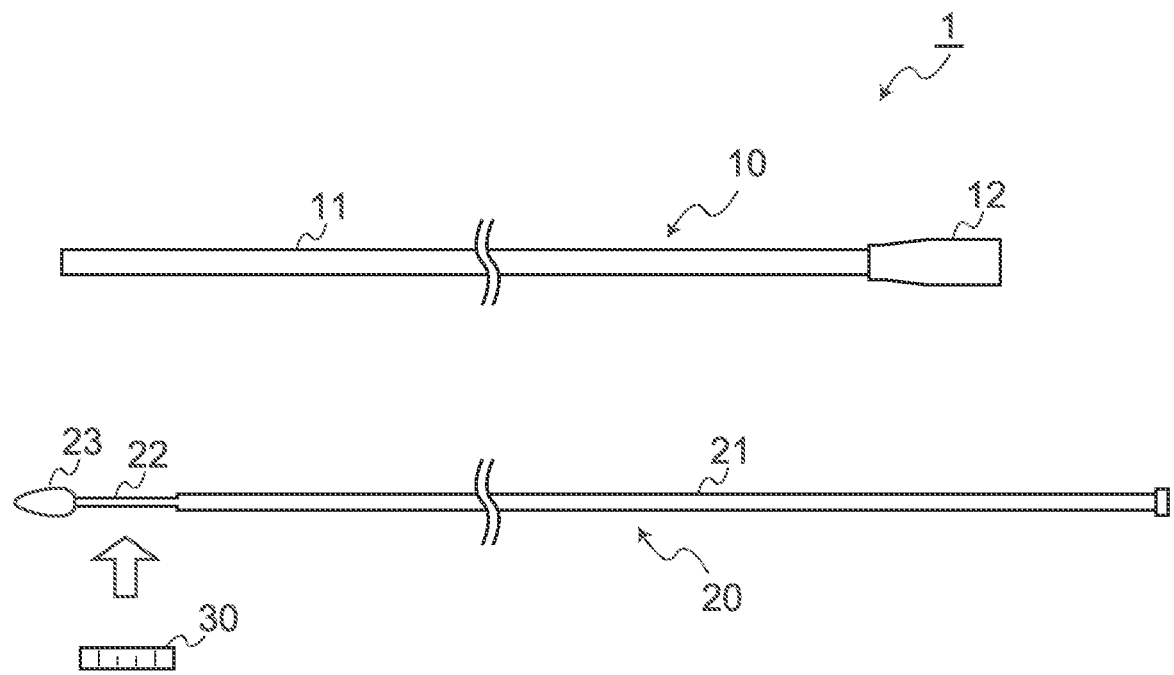
FIG. 1A is a diagram showing the members that constitute a stent graft indwelling device.
Figure 1B:
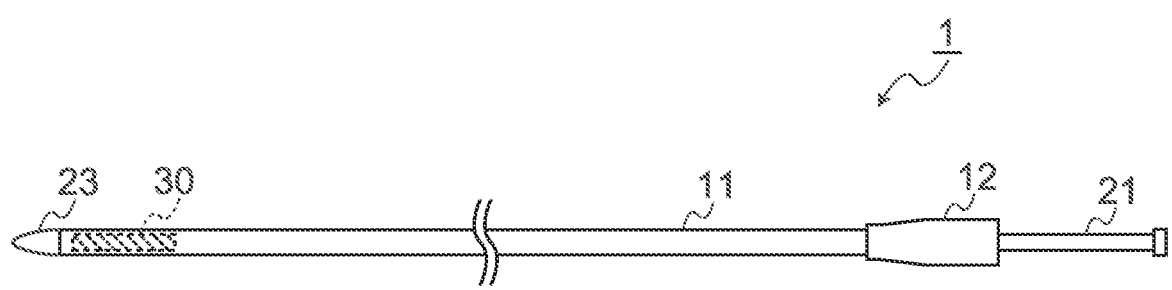
FIG. 1B is a diagram showing the stent graft indwelling device following assembly of the members.

First, the configuration of the stent graft indwelling device 1 according to the embodiment will be described with reference to FIG. 1A and FIG. 1B. In FIG. 1A and FIG. 1B, the size (such as the length and diameter dimension) and shape of the members that constitute the stent graft indwelling device 1 are schematically illustrated. Furthermore, in FIG. 1A and FIG. 1B, the right side of the drawing is referred to as the proximal end side, and the left side of the drawing is referred to as the distal end side.

As shown in FIG. 1A and FIG. 1B, the stent graft indwelling device 1 includes a tubular sheath 10, an inner rod 20 disposed on the inside of the sheath 10 which is capable of advancing and retreating inside the sheath 10 along the axial direction (longitudinal direction) of the sheath 10, and a stent graft 30. The stent graft indwelling device 1 is an indwelling device used, for example, to implant a stent graft inside a blood vessel of the thoracic aorta.

The sheath 10 includes a tubular sheath body 11, and a hub 12 provided on the proximal end side of the sheath body 11. Although not illustrated in the drawings, the hub 12 is provided with a nut for securing the inner rod 20 to the sheath 10 and for releasing the secured state.

The sheath 10 is formed of a flexible material. Examples of the flexible material include biocompatible synthetic resins (elastomers) selected from fluororesins, polyamide-based resins, polyethylene-based resins, polyvinyl chloride-based resins and the like; resin compounds in which another material is mixed with these resins; multilayered structures made of these synthetic resins; and composites of these synthetic resins and metal wires.

The inner rod 20 includes a rod-shaped rod body 21, a holder 22 that holds the stent graft 30 in a contracted state, and a distal end tip 23 provided on the end of the inner rod 20 on the distal end side. The diameter of the holder 22 is, for example, set to be narrower than that of the rod body 21 by the amount of the thickness of the stent graft 30.

Examples of the material forming the rod body 21 and the holder 22 include various materials having appropriate hardness and flexibility, such as resins (plastics or elastomers) and metals. Examples of the material forming the distal end tip 23 include various materials having appropriate hardness and flexibility, such as synthetic resins (elastomers) selected from polyamide-based resins, a polyurethane-based resins, polyvinyl chloride-based resins and the like.

Although not illustrated in the drawings, the rod body 21, the holder 22, and the distal end tip 23 are provided with, for example, a guide wire lumen for passing a guide wire, a trigger wire lumen for passing a trigger wire for expanding the stent graft 30 in the contracted state at the treatment site, and the like, which are formed along the axial direction (longitudinal direction) of the inner rod 20.

Next, the configuration of the stent graft 30 according to the embodiment will be described with reference to FIG. 2A and FIG. 2B, as well as FIG. 3A and FIG. 3B. In the drawings, the thickness and width dimensions and the like of the graft section 40 and the side surface opening 42 of the stent graft 30 are illustrated exaggerated. Furthermore, the framework section 31 is not illustrated in FIG. 2B in order to clearly depict the partial region 41A of the tube wall 41.

Figure 2A:
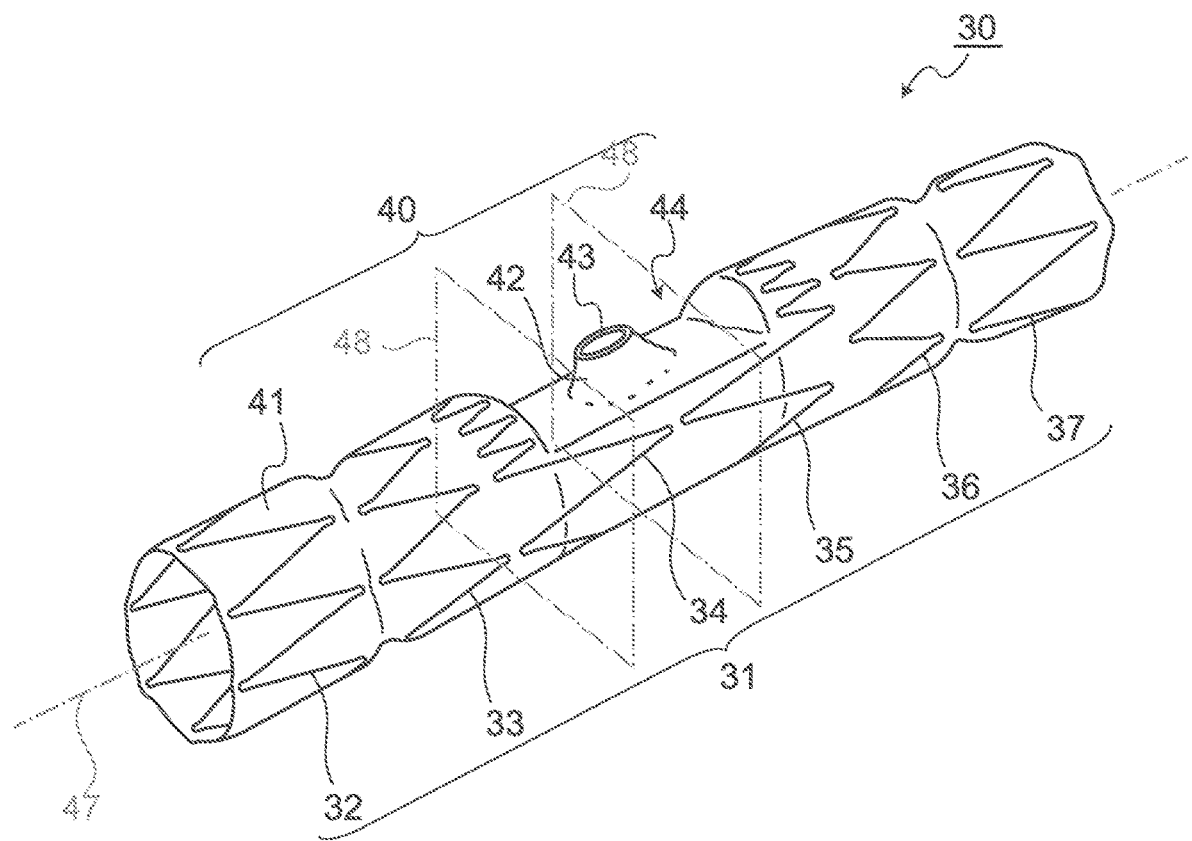
FIG. 2A is a perspective view of the stent graft.
Figure 2B:
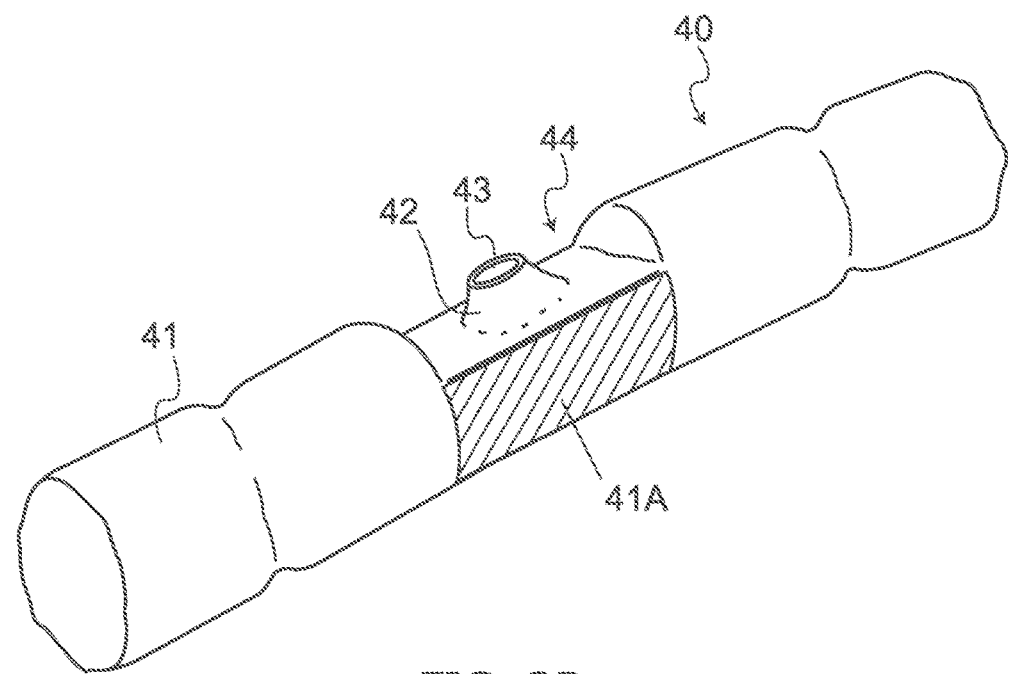
FIG. 2B is a perspective view of the stent graft, and is a diagram schematically showing a partial region that excludes the side surface opening.

As shown in FIG. 2A, the stent graft 30 has, for example, a tubular shape, and includes a framework section 31, and a graft section 40 which is sutured and fixed along the framework section 31.

The framework section 31 is a self-expandable stent framework that has six frame bodies 32 to 37 in which thin metal wires are folded in a zigzag shape, and is formed in a tubular shape. The framework section 31 is configured so as to be deformable from a contracted state, which is inwardly contracted in the radial direction, to an expanded state, which is outwardly expanded in the radial direction.

Examples of the material constituting the framework section 31 (frame bodies 32 to 37) include known metals or metal alloys represented by stainless steel, nickel-titanium alloy, cobalt-chromium alloy, titanium alloy, and the like.

The graft section 40 is sutured and fixed to the framework section 31, and defines a tubular channel. The graft section 40 may cover the framework section 31 from the outer periphery, may cover the framework section 31 from the inner periphery, or may cover the framework section 31 by sandwiching the framework section 31 from both the outer periphery and the inner periphery. Examples of the material of the graft section 40 include fluorine resins such as PTFE (polytetrafluoroethylene) and polyester resins such as polyethylene terephthalate. As the means of fixing the graft section 40 to the framework section 31, for example, the graft section 40 may be fixed to the framework section 31 by welding a section of the graft section 40 to the framework section 31.

As shown in FIG. 2A, a concave section 44, in which a section of the tube wall 41 is recessed inside in a radial direction, is formed in a section of the graft section 40 (an intermediate position of the graft section 40). As shown in FIG. 3A, the concave section 44 has a flat bottom surface 45 and a semilunar side surface 46. Furthermore, the concave section 44 is provided with a side surface opening 42 that allows a lumen region partitioned by the tube wall 41 to communicate with an outer region of the stent graft 30.

The side surface opening 42 has a cylindrical shape protruding from the tube wall 41 of the graft section 40 (the bottom surface 45 of the concave section 44) toward the outer radial direction of the graft section 40, and is formed having a through hole 43 that penetrates the tube wall 41 (bottom surface 45). The side surface opening 42 is arranged at a central position in the bottom surface 45 of the concave section 44 of the graft section 40. The side surface opening 42 is integrally formed with the same material as the graft section 40.

As shown in FIG. 2A, the six frame bodies 32 to 37 constituting the framework section 31 are formed by folding thin metal wires into a zigzag shape. Among the six frame bodies 32 to 37, the frame bodies 34 and 35 that are arranged correspondingly to the side surface opening 42 have a different shape to that of the other frame bodies 32, 33, 36 and 37. That is to say, the frame bodies 32, 33, 36 and 37 that are not arranged correspondingly to the side surface opening 42 have, for example, an annular shape, and the length from one folded section to the next folded section is constant. On the other hand, the frame bodies 34 and 35 that are arranged correspondingly to the side surface opening 42 do not have a constant length from one folded section to the next folded section.

In the present invention, "the frame bodies that are arranged correspondingly to the side surface opening" refer to those frame bodies such as the frame bodies 34 and 35 that intersect a virtual plane 48, when the stent graft 30 is cut by the virtual plane, the virtual plane being orthogonal to the tube axis 47 and passing through the formation region (here, the concave section 44) of the side surface opening 42.

Figure 3A:
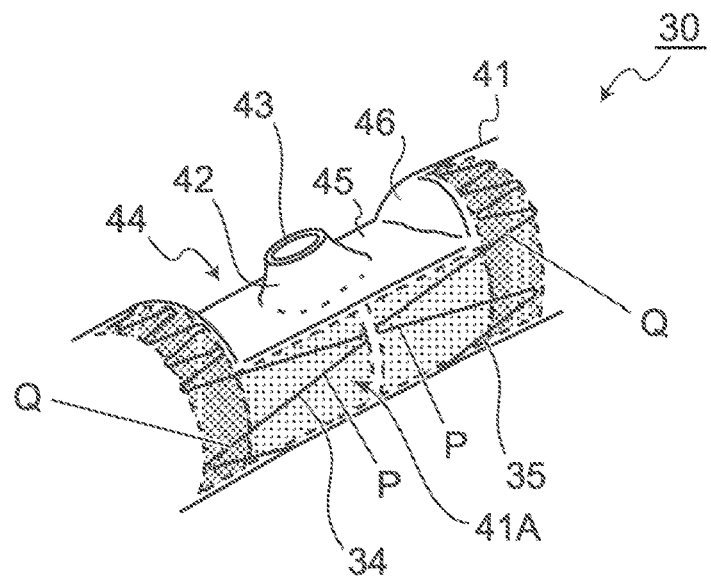
FIG. 3A is a perspective view schematically showing a non-full circumferential section and a full circumferential section of a frame body.
Figure 3B:
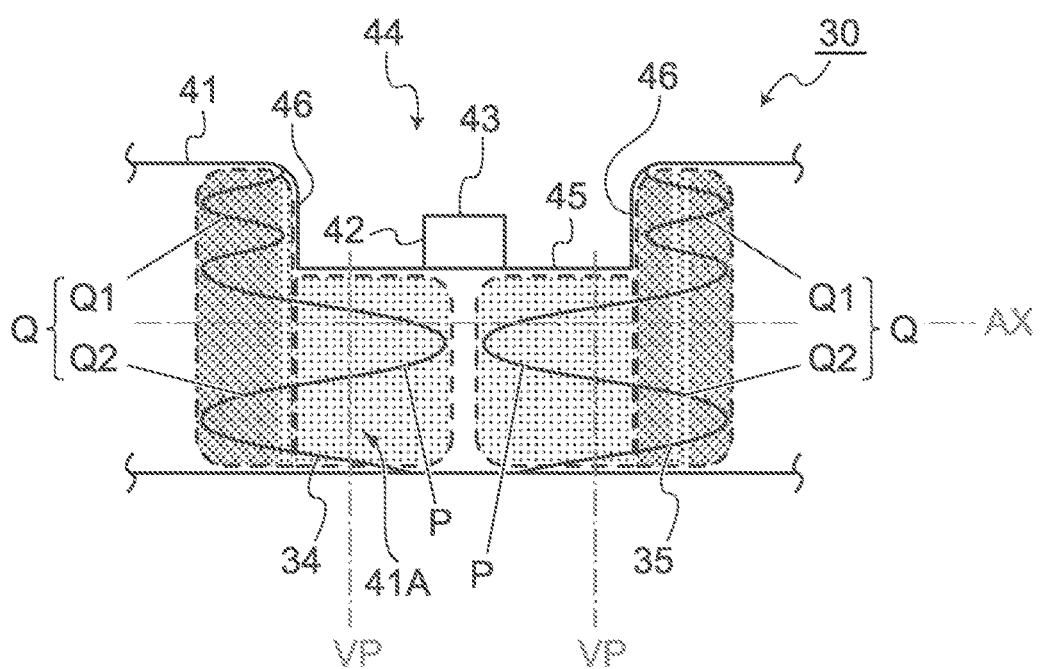
FIG. 3B is a side view schematically showing the non-full circumferential section and the full circumferential section of the frame body.

As shown in FIG. 3A and FIG. 3B, the frame bodies 34 and 35 have a full circumferential section (first frame body structure section) Q, which is present in the tube wall 41 of the graft section 40 along the entire circumference, and a non-full circumferential section (second frame body structure section) P, which is adjacent to the full circumferential section Q and is present in a partial region 41A, which excludes the side surface opening 42 in the circumferential direction of the tube wall 41.

The full circumferential section Q of the frame body 34 is present from the end of the concave section 44 on the distal end side (left side of FIG. 3B) to the distal end side, and the full circumferential section Q of the frame body 35 is present from the end of the concave section 44 on the proximal end side (right side of FIG. 3B) to the proximal end side. Here, the full circumferential section Q is present in the tube wall 41 along the entire circumference, which includes a state where at least a portion (for example, the distal end) of the metal wires that constitute the frame bodies 34 and 35 are arranged in the tube wall 41 so as to overlap in the circumferential direction with a spacing (the vertical direction in the drawing). That is to say, the full circumferential section Q includes a concave section corresponding section Q1, which is present at an end of the concave section 44 in the tube axis direction, and a non-concave section corresponding section Q2, which is continuously formed with the non-full circumferential section P, and with which the entire concave section corresponding section Q1 substantially overlaps in the circumferential direction (the vertical direction in the drawing).

The non-full circumferential section P of the frame bodies 34 and 35 is present below the concave section 44 in FIG. 3B. That is to say, the partial region 41A in which the non-full circumferential section P is present is a region of the peripheral surface of the tube wall 41 that excludes the bottom surface 45 of the concave section 44.

Therefore, of the full circumferential section Q, the sections which are arranged in the region positioned on both tube axis direction sides of the concave section 44 represents a concave section facing section Q1, and the section which are arranged in the region positioned on both tube axis direction sides of the partial region 41A represent a non-concave section facing section Q2, and the concave section facing section Q1 and the non-concave section facing section Q2 are joined by the non-full circumferential section P. Specifically, the concave section corresponding section Q1 of the full circumferential section Q is arranged on the peripheral surface of the tube wall 41 in an arc shape corresponding to the side surface 46 of the concave section 44, and the non-full circumferential section P is arranged so as to be continuous with the end of the concave section facing section Q1 that overlaps with the side surface 46 of the concave section 44 in the circumferential direction. Furthermore, the non-full circumferential section P is folded back below the concave section 44 in FIG. 3B, and the non-concave section corresponding section Q2 is arranged so as to be continuous with the end of the non-full circumferential section P that overlaps with the side surface 46 of the concave section 44 in the circumferential direction. The non-concave section facing section Q2 is folded back at the end which is on the opposite side to the partial region 41A in the tube axis direction, and the non-full circumferential section P is arranged so as to be continuous with the end of the non-concave section corresponding section Q2 that overlaps with the side surface 46 of the concave section 44 in the circumferential direction.

As shown in FIG. 3B, the frame bodies 34 and 35, which are folded in a zigzag shape, have a long section, in which the length from the folded section to the next folded section is long, and a short section. The non-full circumferential section P is configured by a portion of the section in which the length from the folded section to the next folded section is long, and the full circumferential section Q is partially configured by a section in which the length from the folded section to the next folded section is long, and a short section.

The non-full circumferential section P and the full circumferential section Q can be integrally formed by folding the metal wires in a zigzag shape. The non-full circumferential section P and the full circumferential section Q can be connected after individually forming the non-full circumferential section P and the full circumferential section Q.

Next, the configuration of a stent graft set 5 will be described using FIG. 4, as well as FIG. 5A and FIG. 5B.

Figure 4:
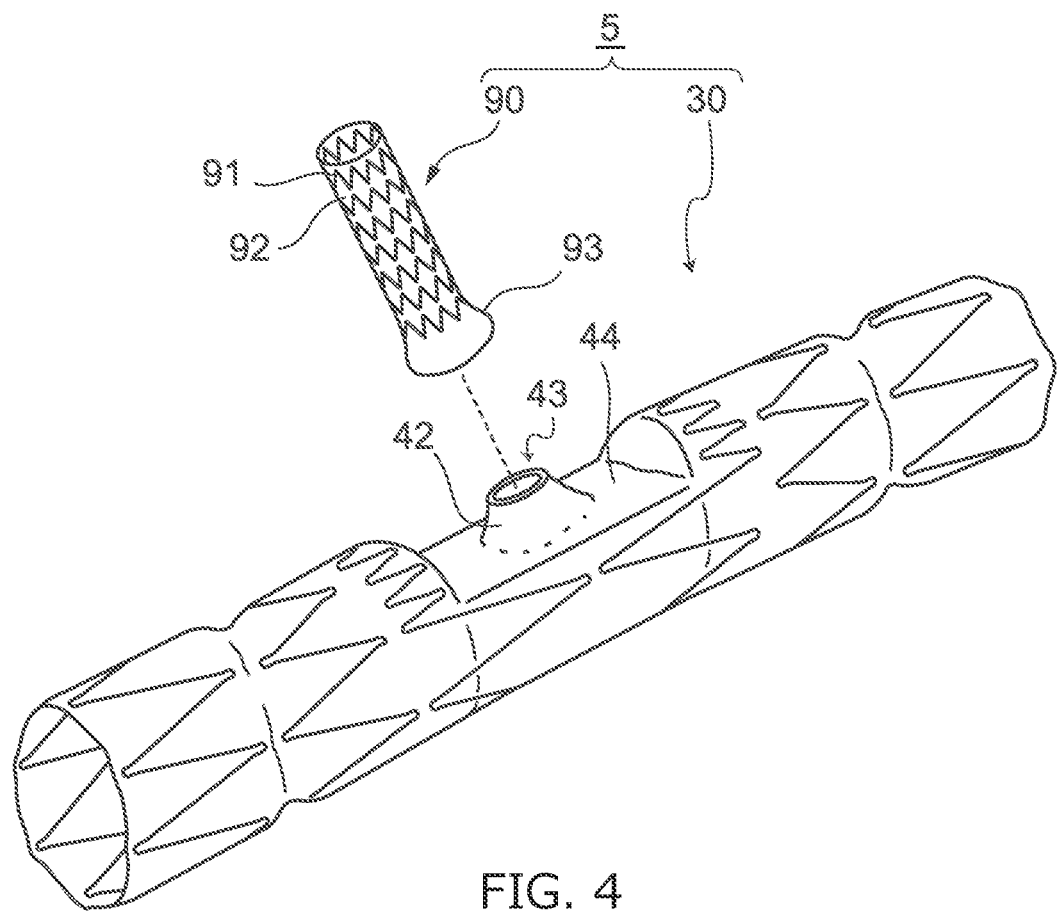
FIG. 4 is a perspective view of a stent graft set.

As shown in FIG. 4, the stent graft set 5 is a combination of a stent graft 30 which is implanted in a main vessel V1, and a stent graft for a branch vessel 90 which is implanted in a branch vessel V2.

The stent graft for a branch vessel 90 is a tubular member having openings at both ends, and similarly to the stent graft 30 described above, defines a tubular passage through which a blood flow can pass. Furthermore, the stent graft for a branch vessel 90 has a smaller diameter than the stent graft 30 described above.

One end 93 of the stent graft for branch vessel 90 has an enlarged diameter shape in which the area of the opening increases approaching the opening end. The stent graft for a branch vessel 90 has, for example, a framework section 91 made of thin metal wires, and a graft section 92 which is fixed to the framework section 91. The configurations of the framework section 91 and the graft section 92 are the same as the framework section 31 and the graft section 40 of the stent graft 30 described above, and a detailed description thereof will be omitted.

Although the configuration of the stent graft 30 is as described above, as shown in FIG. 5A, when the stent graft 30 is implanted in the main vessel V1, the side surface opening 42 is arranged facing the vessel opening of the branch vessel V2. At this time, even if the position of the vessel opening of the branch vessel V1 and the position of the side surface opening 42 of the stent graft 30 do not completely match, the degree of freedom in the orientation and position of the side surface opening 42 is ensured by the non-full circumferential section P, which reduces the likelihood of difficulties occurring when the stent graft for a branch vessel 90 implanted in the branch vessel V2 is attached to the side surface opening 42.

Figure 5A:
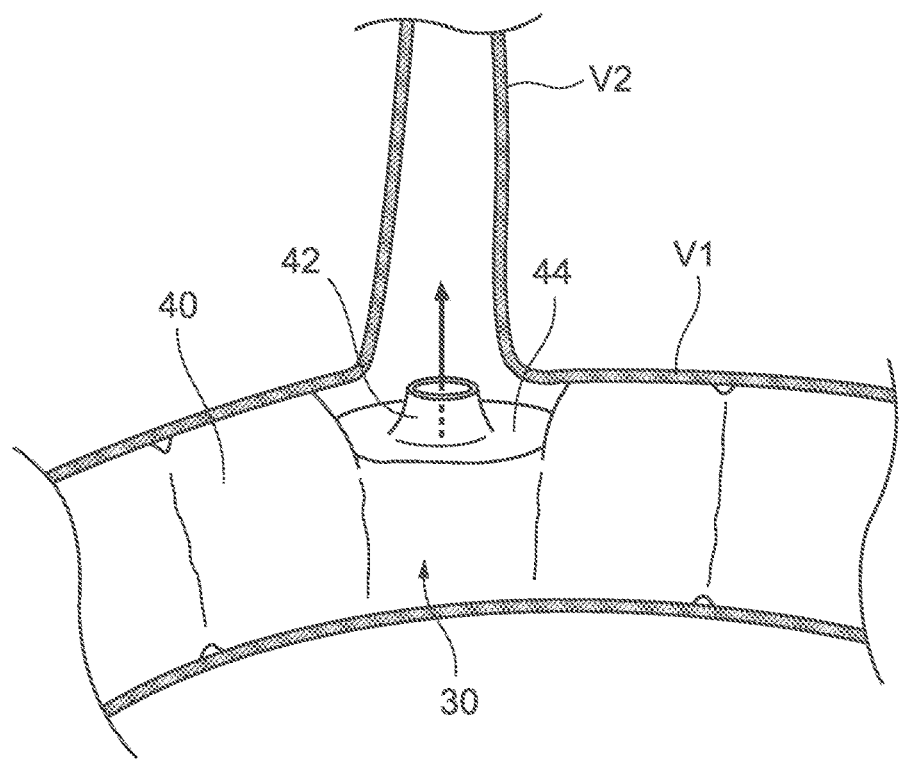
FIG. 5A is a diagram schematically showing a state where the stent graft has been implanted inside a blood vessel.
Figure 5B:
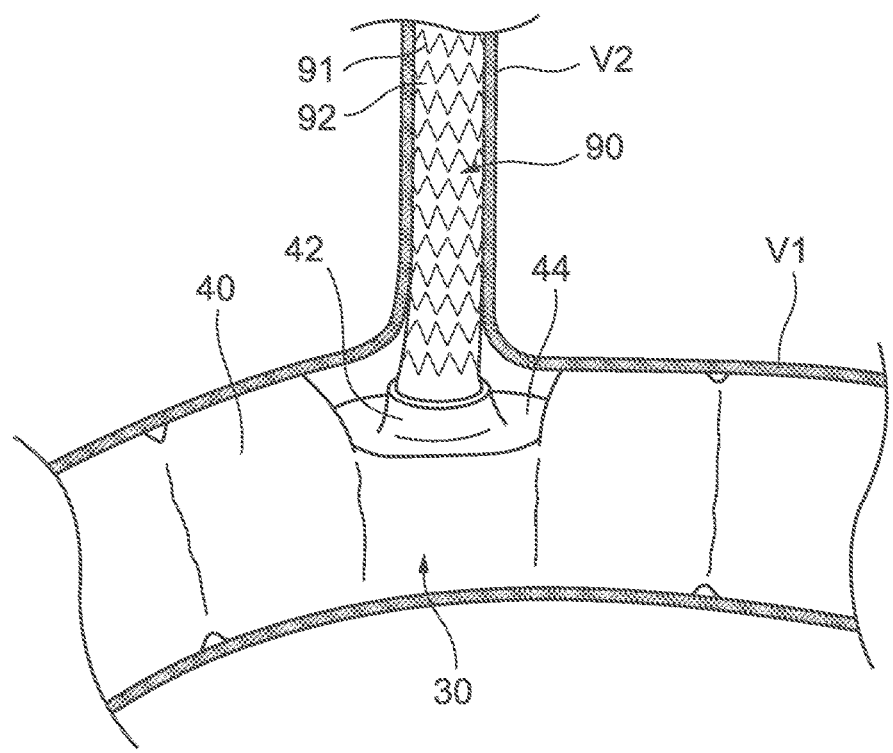
FIG. 5B is a diagram schematically showing a state where a stent graft for a branch vessel has been attached to the stent graft.

Further, when the stent graft for a branch vessel 90 is attached to the side surface opening 42 of the stent graft 30, for example, as shown in FIG. 5A and FIG. 5B, the stent graft for a branch vessel 90 in the contracted state is positioned being passed through the side surface opening 42 from the inside of the stent graft 30, which has been expanded inside the main vessel V1, followed by expansion of the stent graft for a branch vessel 90. At this time, although not illustrated in the drawings, the stent graft for a branch vessel 90 is implanted so that the inner surface of the side surface opening 42 of the stent graft 30 and the outer surface of the one end 93 of the stent graft for a branch vessel 90 are in contact with each other.

According to the stent graft 30 of the embodiment configured as described above, as a result providing the non-full circumferential sections P of the frame bodies 34 and 35 that are present in the partial region 41A, which excludes the side surface opening 42 in the circumferential direction of the tube wall 41, the flexibility near the side surface opening 42 can be maintained. For example, the tolerance can be increased with respect to positional displacement between the side surface opening 42 of the stent graft 30, which is implanted at a branch position between the main vessel V1 and the branch vessel V2, and the vessel opening of the branch vessel V2, and therefore, the adjustment of the orientation and position of the side surface opening 42 with respect to the branch vessel V2 can be simplified.

Furthermore, as a result of providing the full circumferential sections Q, which are adjacent to the non-full circumferential sections P of the frame bodies 34 and 35, the strength of the graft section 40 can be further increased, and displacements of the side surface opening 42 caused by blood flow can be suppressed.

Therefore, the need for highly accurate alignment with a branched tubular tissue (branch vessel V2) is eliminated when implanting the stent graft 30.

Furthermore, by providing the concave section 44 in the tube wall 41 of the graft section 40, a space can be generated between the blood vessel wall of the main vessel V1 and the bottom surface 45 of the concave section 44, and even when the side surface opening 42 is not sufficiently matched with the branch vessel V2, the stent graft for a branch vessel 90 can be implanted such that the side surface opening 42 and the branch vessel V2 are connected inside the space between the blood vessel wall of the main vessel V1 and the bottom surface 45 of the concave section 44.

Furthermore, because the full circumferential section Q is present at the end of the concave section 44 in the tube axis direction, the strength of the graft section 40 can be further increased, and endoleaks can be prevented.

The present invention is not limited to the embodiment described above, and various improvements and design changes may be made without departing from the spirit of the present invention.

Hereinafter, a first to a seventh modification of the stent graft 30 will be described with reference to FIG. 6 to FIG. 12.

Figure 6:
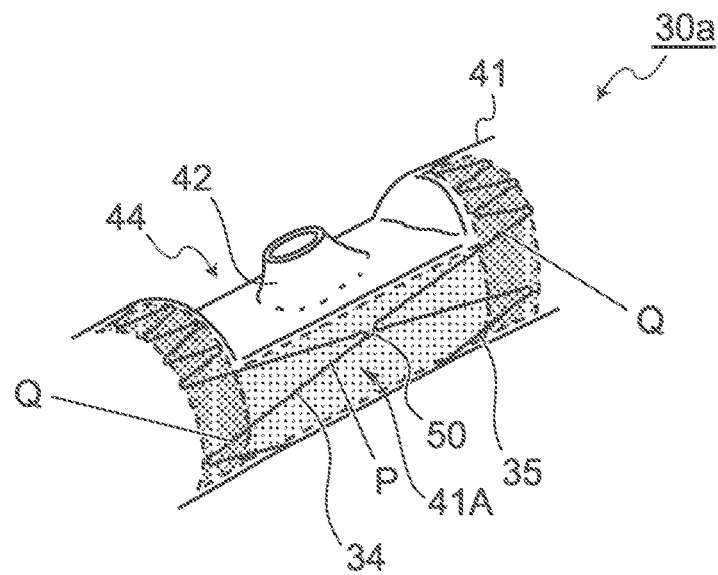
FIG. 6 is a perspective view of a first modification of the stent graft.

In the embodiment described above, although the non-full circumferential sections P of the frame body 34 and the frame body 35 are separated, for example, as illustrated by the stent graft 30a of a first modification shown in FIG. 6, the non-full circumferential sections P of the frame body 34 and the frame body 35 may be integrally formed. Specifically, for example, the non-full circumferential sections P of the frame body 34 and the frame body 35 are integrally formed as a result of the sections (vertices) of the folded sections that are facing each other being connected by a connection member 50. The means by which the non-full circumferential sections P are connected includes, for example, a means whereby a thin metal wire is welded or connected by caulking to the vertices of the zigzag shaped frame body 34 and frame body 35. The connection member 50 is not always necessary, and the frame body 34 and the frame body 35 can be integrally formed by directly welding the vertices.

Figure 7:
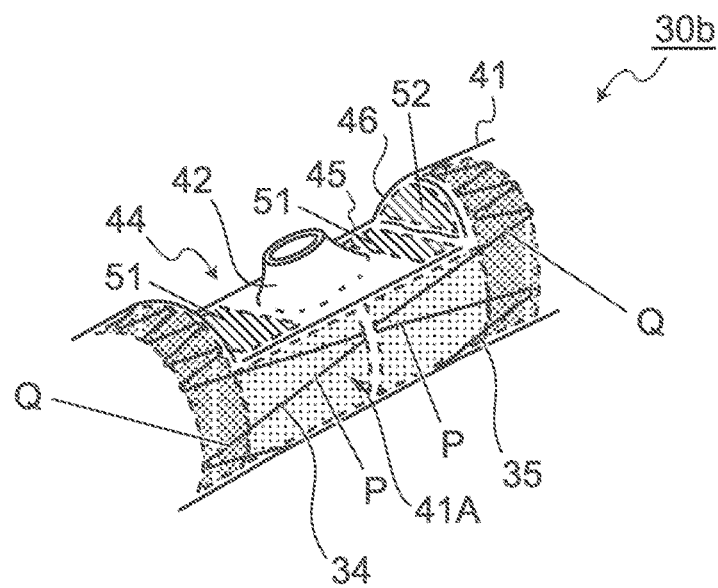
FIG. 7 is a perspective view of a second modification of the stent graft.

Furthermore, although only the side surface opening 42 is provided in the concave section 44 in the embodiment described above, for example, as illustrated by the stent graft 30b of the second modification shown in FIG. 7, the frame bodies 34 and 35 may include, in addition to the non-full circumferential section P and the full circumferential section Q, a bottom surface frame body structure section 51 and a side surface frame body structure section 52 on the bottom surface 45 and the side surface 46 of the concave section 44.

The bottom surface frame body structure section 51 is present at the ends of the concave section 44. The bottom surface frame body structure section 51 only needs to exist in the region excluding the side surface opening 42, and may be arranged so as to surround the side surface opening 42. Furthermore, although the bottom surface frame body structure section 51 and the side surface frame body structure section 52 are both arranged in the stent graft 30b, it is possible for only the bottom surface frame body structure section 51 to be arranged, and for only the side surface frame body structure section 52 to be arranged.

The bottom surface frame body structure section 51 and the side surface frame body structure section 52 are formed, for example, by folding back a thin metal wire in a zigzag shape and then connecting the wires to the frame bodies 34 and 35. The bottom surface frame body structure section 51 and the side surface frame body structure section 52 are not limited to being formed by thin metal wires having a zigzag shape, and they may also have a wave shape or linear shape. Examples of the material that constitutes the bottom surface frame body structure section 51 and the side surface frame body structure section 52 include, similarly to the framework section 31 according to the embodiment, known metals and metal alloys.

Figure 8:
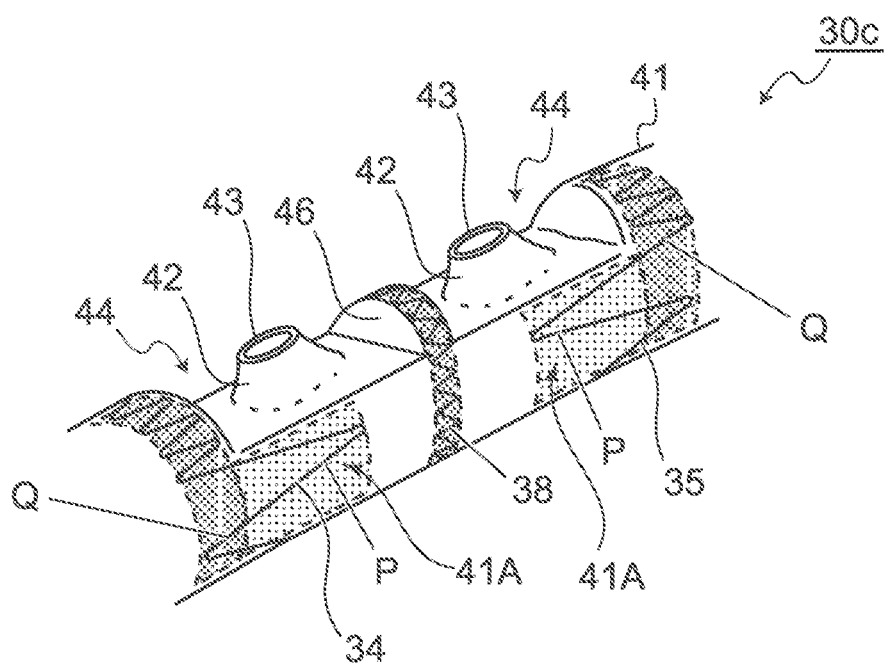
FIG. 8 is a perspective view of a third modification of the stent graft.

Furthermore, the number of side surface openings 42 is not limited to one, and, for example, as illustrated by the stent graft 30c of a third modification shown in FIG. 8, it is possible to include two concave sections 44 and 44, and to provide a side surface opening 42 in each of the concave sections 44. Furthermore, a frame body 38 may be arranged along the entire circumference between the two concave sections 44 and 44.

Although not illustrated, a plurality of side surface openings 42 may be provided in a single concave section 44. In this case, a frame body 38 may be provided along the entire circumference between the plurality of side surface openings 42 that are adjacent to each other.

Figure 9:
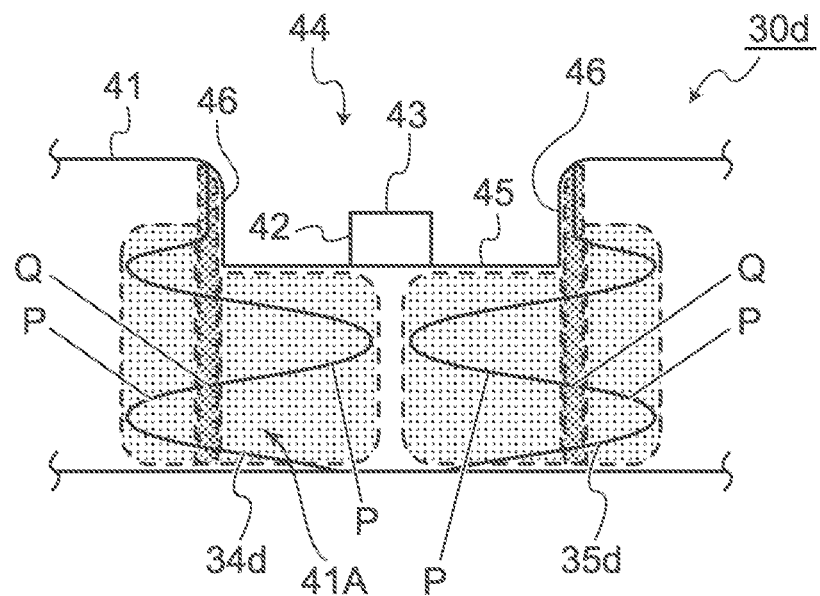
FIG. 9 is a side view of a fourth modification of the stent graft.

Moreover, the shape of the full circumferential section Q is not limited to a zigzag shape, and, for example, as illustrated by the stent graft 30d of a fourth modification shown in FIG. 9, the full circumferential sections Q of the frame bodies 34d and 35d may be configured by a section that extends in the circumferential direction while bending in a zigzag shape, and a section that extends in the circumferential direction in an arc shape.

Figure 10:
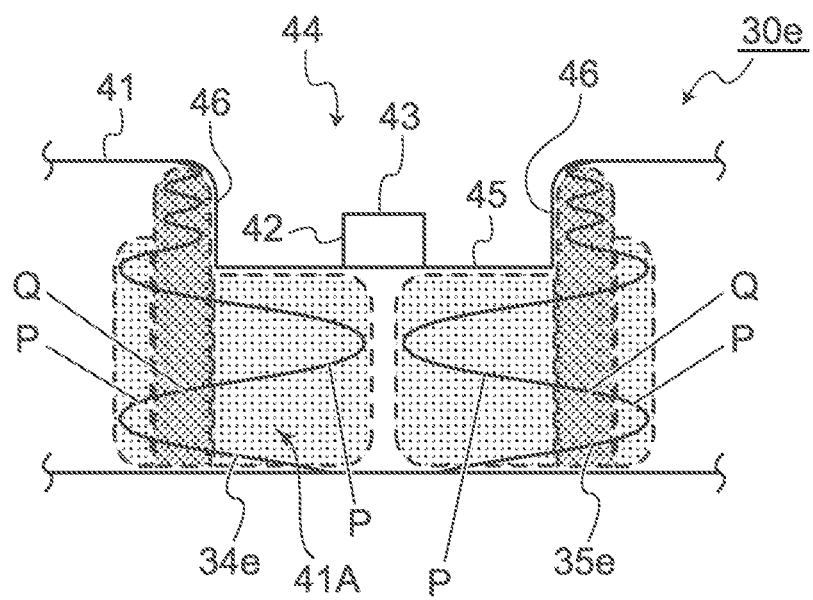
FIG. 10 is a side view of a fifth modification of the stent graft.
Figure 11:
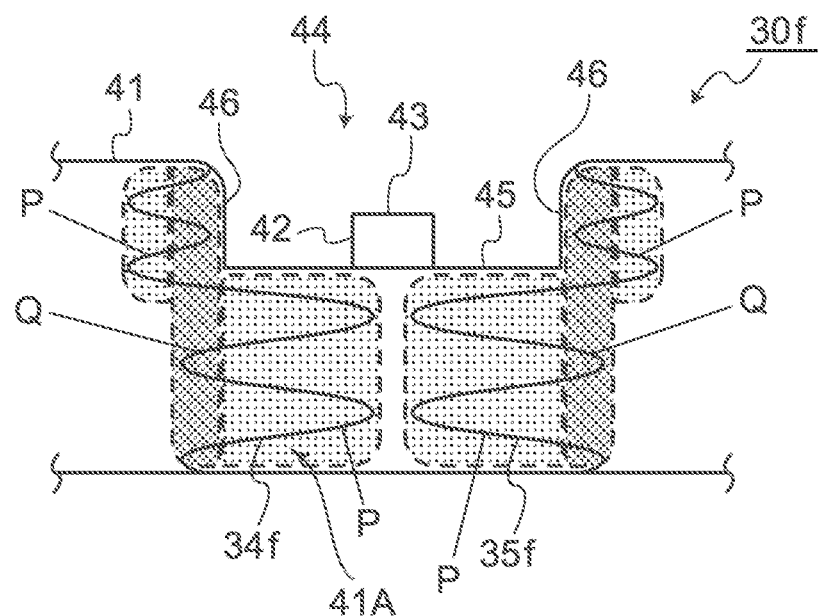
FIG. 11 is a side view of a sixth modification of the stent graft.

In addition, the positions of the full circumferential sections Q are not limited to the end of the frame bodies 34 and 35 in the tube axis direction, and, for example, as illustrated by the stent graft 30e of a fifth modification shown in FIG. 10, the full circumferential sections Q may exist between the non-full circumferential sections P of the frame bodies 34e and 35e. Similarly, for example, as illustrated by the stent graft 30f of a sixth modification shown in FIG. 11, the full circumferential sections Q may exist between non-full circumferential sections P of the frame bodies 34f and 35f. In the fifth modification and the sixth modification, the shapes of the frame bodies 34e, 35e, 34f and 35f formed by thin metal wires having a zigzag shape are different, and, for example, by adjusting the positions of the folded sections of the frame bodies 34e, 35e, 34f and 35f and the length from the folded section to the next folded section, the full circumferential sections Q and the non-full circumferential sections P can be adjusted to appropriate positions.

Figure 12:
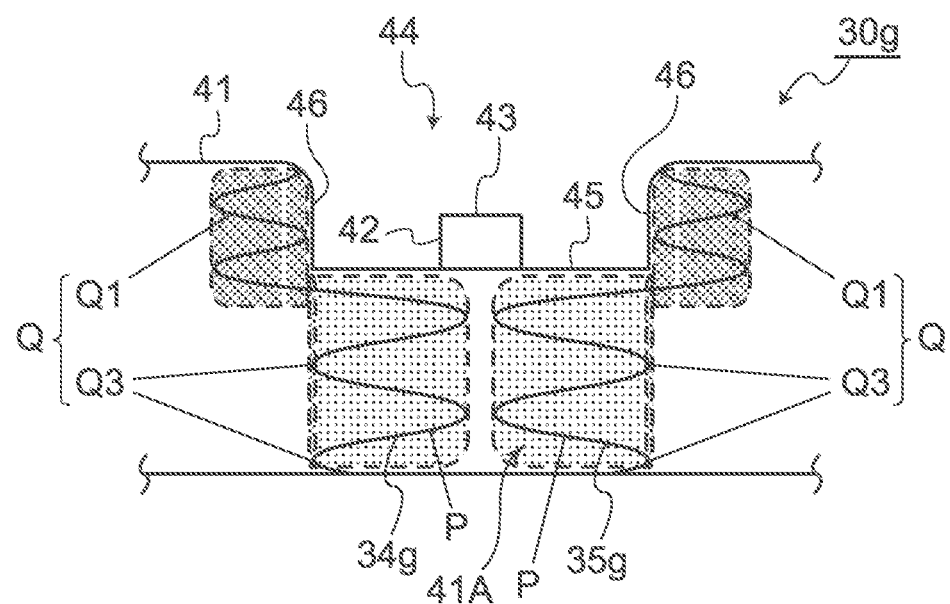
FIG. 12 is a side view of a seventh modification of the stent graft.

Furthermore, as illustrated by the stent graft 30g of a seventh modification shown in FIG. 12, the full circumferential sections Q of the frame bodies 34g and 35g may be configured to include concave section corresponding sections Q1, which are present at the ends of the concave section 44 in the tube axis direction, and bent parts Q3 (a distal end side bent part Q3 in the frame body 34g and a proximal end side bent part Q3 in the frame body 35g) which overlap with the ends of the concave section corresponding sections Q1 on the concave section 44 side in the circumferential direction (the vertical direction in the drawing), and are consecutively formed with the non-full circumferential sections P of the frame bodies 34g and 35g.

As a result, the stent graft 30g is capable of reinforcing the strength of the graft section 40 while maintaining the flexibility near the side surface opening 42, and can suppress large displacements of the side surface opening 42 caused by blood flow.

In the embodiment described above, a stent graft including a framework section made of thin metal wires has been described as an example, but the present invention is not limited to this. For example, the present invention is also applicable to a stent graft including a framework section made of a material other than metal (for example, a ceramic or resin). Furthermore, although a case where the framework section comprises six frame bodies has been described as an example, the present invention is not limited to this, and the framework section may be composed of five or fewer frame bodies, or seven or more frame bodies. In addition, although the embodiment described above presented a self-expanding stent graft as an example, the present invention is not limited to this, and is applicable to a balloon-expandable stent graft.

Although the embodiment described above presented a stent graft provided with frame bodies having a zigzag shape, the present invention is not limited to this. For example, the present invention is also applicable to a stent graft provided with frame bodies having a wave shape. Furthermore, although the embodiment described above presented a case where the non-full circumferential section and the full circumferential section are integrally formed, the present invention is not limited to this, and the non-full circumferential section and the full circumferential section may be assembled after being formed separately.

Moreover, for example, in the stent graft 30b of the second modification shown in FIG. 7, the full circumferential section Q does not have to be included as long as at least a bottom surface frame body structure section 51 is arranged on the bottom surface 45 of the concave section 44, or a side surface frame body structure section 52 is arranged on the side surface 46 of the concave section 44. Even in such a configuration, because the bottom surface frame body structure section 51 and the side surface frame body structure section 52 are present in the region excluding the side surface opening 42, flexibility can be maintained near the side surface opening 42 even when the full circumferential section Q does not exist, which enables the orientation and position of the through hole 43 to be more easily adjusted, which suppresses displacements of the side surface opening caused by blood flow.

In addition, although not illustrated in the drawings, the positions and shapes of the thin metal wires may be different between the distal end side frame body 34 and the proximal end side frame body 35. That is to say, for example, the frame body 34 shown in FIG. 3B may be provided on the upstream side of the blood vessel through which blood flows, and the frame body 35g shown in FIG. 12 may be provided on the downstream side. Therefore, by configuring at least the distal end side (upstream side of the blood flow) frame body 34 to include a full circumferential section Q, which includes a concave section corresponding section Q1 and a non-concave section corresponding section Q2, the strength of the graft section 40 can be appropriately increased, and endoleaks caused by blood flow from the upstream side can be prevented.

On the other hand, in the case of the proximal end side (downstream side of the blood flow) frame body 35, because the aspect of maintaining the flexibility near the side surface opening 42 is considered to be more important than the aspect of preventing endoleaks due to blood flow from the upstream side as in the case of the distal end side (upstream side of the blood flow) frame body 34, it is possible to increase the degree of freedom in the arrangement of the full circumferential section Q and the non-full circumferential section P. That is to say, for example, as illustrated by the stent graft 30g of the seventh modification shown in FIG. 12, the concave section corresponding section Q1 and the non-full circumferential section P may be arranged with a separation in the tube axis direction. For example, a connection section made of a linear thin metal wire may be provided between the concave section corresponding section Q1 and the non-full circumferential section P such that they are integrally formed. Furthermore, the width of the concave section corresponding section Q1 and the non-full circumferential section P in the tube axis direction and the distance between the concave section corresponding section Q1 and the non-full circumferential section P may be appropriately adjusted to conform to the shape of the concave section 44.

Moreover, although the embodiment above has illustrated a case where the graft section is a straight tube shape, the present invention is not limited to this, and the graft section may have a curved shape which takes the form of an arc, or a twisted bent shape. For example, in FIG. 2A, a curved section may be formed such that the end of the stent graft 30 is downwardly bent in the drawing, and a concave section may be formed on the outside section of the bent section of the graft section (the upper section in the drawing).

Furthermore, although the embodiment and the modifications described above illustrated a case where the side surface opening is formed of the same material as the graft section and is integrally formed, the present invention is not limited to this, and the side surface opening and the graft section may be formed of members that are each independent, and the two members may be attached to each other. In this case, the side surface opening may be made of the same material as the graft section, or may be made of a different material. Furthermore, although the embodiment and the modifications described above were illustrated with the side surface opening being provided at a central position of the bottom surface of the concave section, it is not limited to this, and the present invention is applicable to stent grafts in which the side surface opening is provided at the end of the bottom surface or a side surface of the concave section. Moreover, although the embodiment described above illustrated a cylindrically-shaped side surface opening 42 as an example, the present invention is not limited to this. For example, a side surface opening in which only a through hole is provided in the tube wall of the graft is also possible.

Furthermore, although the embodiment and the modifications described above illustrated a case where a concave section is provided, examples are not limited to this, and the tube wall 41 may be provided with a side surface opening without providing a concave section.

In addition, although above embodiment described above presented an example of a stent graft for the thoracic aorta, examples are not limited to this, and application is also possible with respect to a stent graft for the abdominal aorta, or a stent graft for the thoracic abdominal aorta. Moreover, the present invention is also applicable to stent graft intended to be implanted in organs other than a blood vessel (such as the digestive tract or the bile duct).

The disclosure of Japanese Patent Application No. 2017-227227, filed Nov. 27, 2017, including the specification, drawings and abstract, is incorporated herein by reference in its entirety.

DESCRIPTION OF REFERENCE NUMERALS

1 Stent graft indwelling device
30, 30a, 30b, 30c, 30d, 30e, 30f, 30g Stent graft
5 Stent graft set
90 Stent graft for branch vessel
V1 Main vessel
V2 Branch vessel
31 Framework section
32, 33, 34, 35, 34d to 34g, 35d to 35g, 36, 37, 38 Frame body
40 Graft section
41 Tube wall
41A Partial region
42 Side surface opening
44 Concave section
Q Full circumferential section (first frame body structure section)
P Non-full circumferential section (second frame body structure section)

The invention claimed is:

1. A stent graft comprising: a framework section including a plurality of frame bodies; and a tubular graft section that is fixed to the framework section, wherein, in a part of a tube wall of the tubular graft section, a concave section recessed in a radial direction is provided, a side surface opening that passes through to a lumen of the tubular graft section is provided in the concave section, wherein the tube wall is divided into a first tube wall section in which the concave section is not provided and a second tube wall section in which the concave section is provided, in a direction of a tube axis of the tubular graft section, wherein the plurality of frame bodies are arranged along the tube axis of the tubular graft section, and a first frame body, among the plurality of frame bodies, is arranged correspondingly to the side surface opening, such that the first frame body includes a first frame body structure section that is disposed in the first tube wall section and a second frame body structure section that is disposed in a part of the second tube wall section not including the side surface opening, wherein the first frame body is formed by a single wire folded in a zigzag shape, said single wire having folded sections, and said first frame body intersects a virtual plane, wherein the virtual plane is orthogonal to the tube axis and passes through the concave section, wherein the single wire has a long section and a short section, wherein a distance between folded sections in the long section is greater than a distance between folded sections in the short section, wherein the long section extends from the first tube wall section to the second tube wall section to form the second frame body structure section and a portion of the first frame body structure section, and wherein the short section extends only in the first tube wall section to form a portion of the first frame body structure section.

2. The stent graft according to claim 1, wherein said tubular graft section includes a curved portion and wherein the concave section is provided on an outside section of said curved section.

3. A stent graft indwelling device comprising the stent graft according to claim 1, wherein the stent graft is configured to expand in a radial direction.

4. The stent graft according to claim 1, wherein said concave section does not extend around the entire circumference of said second tube wall section, said framework section extending from a portion of said tubular graft section without said radially-directed recess to a portion of said tubular graft section with said radially-directed recess.

5. The stent graft according to claim 1, wherein said first tube wall section has a first diameter and said second tube wall section has a second diameter equal to said first diameter.

6. The stent graft according to claim 1, wherein said framework section includes a single contiguous wire disposed in both said first and second tube wall sections.

7. The stent graft according to claim 1, wherein said framework section includes a single contiguous wire, wherein a first portion of said single contiguous wire extends axially along said first tube wall section and wherein a second portion of said wire extends axially along said second tube wall section, and wherein the amount of axial extension of said wire along said second frame body structure section is greater than the amount of axial extension of said wire along said first frame body structure section.

8. The stent graft according to claim 1, wherein said second tube wall section includes first, second, and third axial portions, wherein said second axial portion is positioned between said first and third axial portions, wherein there is a gap between frame bodies fixed to said first and third axial portions, and wherein said gap overlaps said concave section.

9. The stent graft according to claim 1, wherein said second tube wall section includes a first portion fixed to said first frame body and a second section fixed to a second frame body of said plurality of frame bodies.

10. A stent graft comprising:
a framework section including a plurality of frame bodies; and
a tubular graft section that is fixed to the framework section, said tubular graft section including a tube wall and having a longitudinal axis;
wherein said tube wall includes a concave section recessed in a radial direction and wherein said concave section includes a side surface opening that passes through to a lumen of the tubular graft section;
wherein the tube wall is divided in a direction of said longitudinal axis into a first tube wall section in which the concave section is not provided and a second tube wall section in which the concave section is provided;
wherein the plurality of frame bodies includes first and second structural bodies, said first tube wall section fixed to said first structural body and said second tube wall section fixed to said second structural body, and wherein said first structural body is connected to said second structural body,
wherein the first and second structural bodies are each formed by a wire folded in a zigzag shape, said wire having folded sections, and said first and second structural bodies each intersects a virtual plane that is orthogonal to the tube axis, a virtual plane passing through said second structural body passing through said concave section, wherein the first structural body has a first section and a second section, wherein a distance between folded sections in the first section is greater than a distance between folded sections in the second section, wherein the first section of the first structural body extends from the first tube wall section up to the second tube wall section and wherein the second section of the first structural body extends along only the first tube wall section, wherein second structural body has a third section, wherein a distance between folded sections in the third section is equal to the distance between folded sections in the first section of the first structural body, and wherein the folded sections of the third section of the second structural body are connected to folded sections of the first section of the first structural body.

11. The stent graft according to claim 10, wherein said framework section includes a single contiguous wire disposed in both said first and second tube wall sections.

12. The stent graft according to claim 10, wherein said framework section includes a single contiguous wire, wherein a first portion of said single contiguous wire extends axially along said first tube wall section and wherein a second portion of said wire extends axially along said second tube wall section, and wherein the amount of axial extension of said wire along said second tube wall section is greater than the amount of axial extension of said wire along said second section of said first structural body.

13. The stent graft according to claim 10, wherein said second tube wall section includes first, second, and third axial portions, wherein said second axial portion is positioned between said first and third axial portions, wherein there is a gap between frame bodies fixed to said first and third axial portions, and wherein said gap overlaps said concave section.

14. A stent graft comprising:
a tubular stent body having a longitudinal axis, said tubular stent body including first and second portions disposed axially relative to each other, said second portion including a section recessed in a radial direction, wherein said first and second sections have respective first and second circumferences and wherein said first circumference is identical to said second circumference except at said recessed section;

a reinforcing element fixed to said first and second portions, wherein said reinforcing element extends from said first portion to said second portion, wherein the reinforcing element is formed by a single wire folded in a zigzag shape, said single wire having folded sections, and said reinforcing element intersects a virtual plane, wherein the virtual plane is orthogonal to the tubular stent body longitudinal axis and passes through the radially recessed section, wherein the single wire has a long section and a short section, wherein a distance between folded sections in the long section is greater than a distance between folded sections in the short section, wherein the long section extends from the first tubular stent body portion to the second tubular stent body portion, and wherein the short section extends only in the first tubular stent body portion.

15. The stent graft according to claim 14, wherein said reinforcing element includes a single contiguous wire disposed in both said first and second portions of said tubular stent body.

16. The stent graft according to claim 14, wherein said reinforcing element includes a single contiguous wire, wherein a first portion of said single contiguous wire extends axially along said first portion of said tubular stent body and wherein a second portion of said wire extends axially along said second portion of said tubular stent body portion, and wherein the amount of axial extension of said wire along said second portion of said tubular stent body is greater than the amount of axial extension of said short section of said wire along said first portion of said tubular stent body.

17. The stent graft according to claim 14, wherein said second portion of said tubular stent body includes first, second, and third axial portions, wherein said second axial portion is positioned between said first and third axial portions, wherein there is a gap between reinforcing elements fixed to said first and third axial portions, and wherein said gap overlaps said radially-directed recessed section.

* * * * *